US00PP09960P

United States Patent [19]

Bradford et al.

[11] Patent Number: Plant 9,960

[45] Date of Patent: Jul. 15, 1997

[54] NECTARINE TREE 'GRAND PEARL'

[76] Inventors: Lowell Glen Bradford, 12439 E. Savana Rd.; Norman G. Bradford, 11875 E. Savana Rd., both of Le Grand, Calif. 95333

[21] Appl. No.: 642,892

[22] Filed: May 6, 1996

[51] Int. Cl.[6] ..... A01H 5/00

[52] U.S. Cl. ..... Plt./40.1

[58] Field of Search ..... Plt./40.1

[56] References Cited

U.S. PATENT DOCUMENTS

P.P. 7,193 3/1990 Bradford et al. ..... Plt./41.1
P.P. 9,360 11/1995 Bradford et al. ..... Plt./40.1

*Primary Examiner*—James R. Feyrer

[57] ABSTRACT

The present invention relates to a nectarine, *Prienus persica* tree and more particularly to a new and distinct variety broadly characterized by a medium size, medium vigorous, productive and regular bearing tree. The fruit matures under the ecological conditions described approximately the second week in July, with first picking on Jul. 8, 1995. The fruit is uniformly medium in size, subacidic in flavor, globose in shape, clingstone in type, very firm in texture, and dark red in skin color. The variety was a first generation cross using Red Glen (U.S. Plant Pat. No. 7,193) yellow flesh nectarine as the selected seed parent and June Pearl (U.S. Plant Pat. No. 9,360) white flesh nectarine as the selected pollen parent.

1 Drawing Sheet

BACKGROUND OF THE VARIETY

In a continuing effort to improve the quality of fresh market and shipping fruits, we, the inventors, typcially hybridize a large number of nectarine and peach seedlings each year. The present invention relates to a new and distinct variety of nectarine tree, which has been denominated varietally as "Grand Pearl". The present variety was developed by us in 1992 in a cultivated area of our experimental orchard at Bradford Farms near Le Grand, Calif. in Merced County (San Joaquin Valley). It was a first generation cross using Red Glen (U.S. Plant Pat. No. 7,193) yellow flesh mectarine as the seed parent and June Pearl (U.S. Plant Pat. No. 9,360) white flesh nectarine as the selected pollen parent. Subsequent to origination of the present variety of nectarine tree, we asexually reproduced it by budding and grafting, and such reproduction of plant and fruit characteristics were true to the original plant in all respects.

The fruit produced by the present variety is most similar to its pollen parent, the June Pearl (U.S. Plant Pat. No. 9,360), by producing white flesh clingstone nectarines that are subacidic in flavor, medium in size, full red in skin color and almost free of red texture bleeding, but is distinguished therefrom and an improvement thereon by producing fruit that ripens about four weeks later, that is firmer in texture, that is sweeter in flavor, and that is less prone to protruding at the apex.

The present variety is similar to its seed parent, Red Glen (U.S. Plant Pat. No. 7,193) by producing very firm, full red clingstone nectarines, but is very distinguished therefrom by producing fruit that is white flesh instead of yellow flesh, that ripens about about 2 weeks earlier, and that is subacidic in flavor instead of acidic.

DRAWING

The accompanying photograph exhibits three whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jul. 12, 1995. All major color code designations are by reference to the Inter-Society Color Council, National Bureau of Standards. Common color names are also used occasionally.

TREE

Size: Medium.
Vigor: Medium.
Growth: Spreading and dense.
Form: Round topped.
Hardiness: Hardy.
Production: Productive.
Bearing: Regular bearer.
Trunk:
- *Size.*—Medium.
- *Texture.*—Medium.
- *Bark color.*—Dark brown [59. d.Br].
- *Lenticels.*—Numerous. Color: Light brown [57. l.Br]. Average size: 1⅛" to ⅜" [3.2–9.5 mm.].

Branches:
- *Size.*—Medium.
- *Texture.*—Medium.
- *Color.*—1st year wood topside: Grayish pink [8. gy.Pk]. 1st year wood underside: Strong yellow green [117. s.YG]. Older wood: Strong yellowish brown [74. s.yBr].
- *Lenticels.*—Numerous, small. Color: Strong orange yellow [68. s.OY]. Average size: 1/16" [1.6 mm.].

Leaves:
- *Size.*—Medium. Average length: 5½" [139.7 mm]. Average width: 1 7/16" [36.5 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125. m.OlG]. Ventral surface: Moderate yellow green [120. m.YG].

*Margin.*—Finely serrate.
*Venation.*—Pinnately net veined.
*Petiole.*—Average length: ½" [12.7 mm]. Average thickness: 1/16" [1.6 mm]. Color: Moderate yellow green [120. m.YG].
*Stipules.*—Numerous. Average length: 7/16" [11.1 mm].
*Glands.*—Numbers: 2 to 4 per leaf. Position: Alternately positioned on petiole and base of blade. Size: Medium. Form: Reniform. Color: Brilliant yellow green [116. brill.YG].

Flower buds:
*Hardiness.*—Hardy.
*Size.*—Medium.
*Length.*—Medium.
*Form.*—Free.
*Surface.*—Pubescent.

Flowers:
*Blooming period.*—Medium to late as compared with other varieties.
*Size.*—Large.
*Color.*—Pale purplish pink [252. p.pPk].

FRUIT

Maturity when described: Firm eating ripe, Jul. 12, 1995.
Date of first picking: Jul. 8, 1995.
Date of last picking: Jul. 17, 1995.
Size: Uniform, medium.
*Average diameter axially.*—2 9/16" [65.1 mm.].
*Average transversely in suture plane.*—2 9/16" [65.1 mm.].
Form: Globose to ovate, uniform, symmetrical.
*Longitudinal section form.*—Round.
*Transverse section through diameter.*—Oval.
Suture: An inconspicuous line extending from the base to beyond the apex, having a slight depression beyond the pistil point, and becoming a fairly sharp groove very close to the stem.
Ventral surface: Rounded, lipped toward the apex.
Lips: Slightly unequal.
Cavity: Flaring, circular, with some stem markings typical.
*Depth.*—⅜" [9.5 mm.].
*Breadth.*—⅞" [22.2 mm.].
Base: Rounded to truncate.
Apex: Rounded.
Pistil point: Negligible in length, apical and depressed within the suture.
Stem: Medium.
*Average length.*—⅜" [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—Slight in the wet season.
*Color.*—Dark red [16. d.R] blending to strong red [12. s.R] with light yellowist brown [76. l.yBr] freckling toward the apex.
Flesh:
*Color.*—White [263. White] to pale yellow green [121. p.YG] with some deep red [13. deep R] streaking very close to the stone.
*Surface of pit cavity.*—Clingstone.
*Amygdalin.*—Wanting.
*Juice.*—Abundant, rich.
*Texture.*—Very firm, tough, crisp.
*Fibers.*—Abundant, fine.
*Ripens.*—Evenly.
*Flavor.*—Subacidic and sweet, with 16 to 18 brix.
*Aroma.*—Moderate.
*Eating quality.*—Very best.

STONE

Type: Clingstone.
Form: Oval.
Base: Straight.
Apex: Acute.
Sides: Equal.
Surface: Irregularly furrowed toward the apex and pitted toward the base.
Ridges: Jagged toward the base.
Color: Moderate brown [58. m.Br].
Pit wall: ¼" [6.4 mm.] thick.
Tendency to split: None observed.
Kernel:
*Form.*—Oval.
*Taste.*—Bitter.
*Viable.*—Yes.
*Average width.*—7/16" [11.1 mm.].
*Average length.*—11/16" [17.5 mm.].
*Skin color.*—Brilliant orange yellow [67. brill.OY] with moderate brown [58. m.Br] veins running from the pellicle to the apex.
*Pellicle color.*—Grayish brown [61. gy.Br].
*Amygdalin.*—Abundant.

USE

Market: Fresh and long distance shipping.
Keeping quality: Very good.
Shipping quality: Very good.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its pollen parent, the June Pearl (U.S. Plant Pat. No. 9,360), by producing white flesh clingstone nectarines that are subacidic in flavor, medium in size, full red in skin color and almost free of red texture bleeding, but is distinguished therefrom and an improvement thereon by producing fruit that ripens about four weeks later, that is firmer in texture, that is sweeter in flavor, and that is less prone to protruding at the apex.

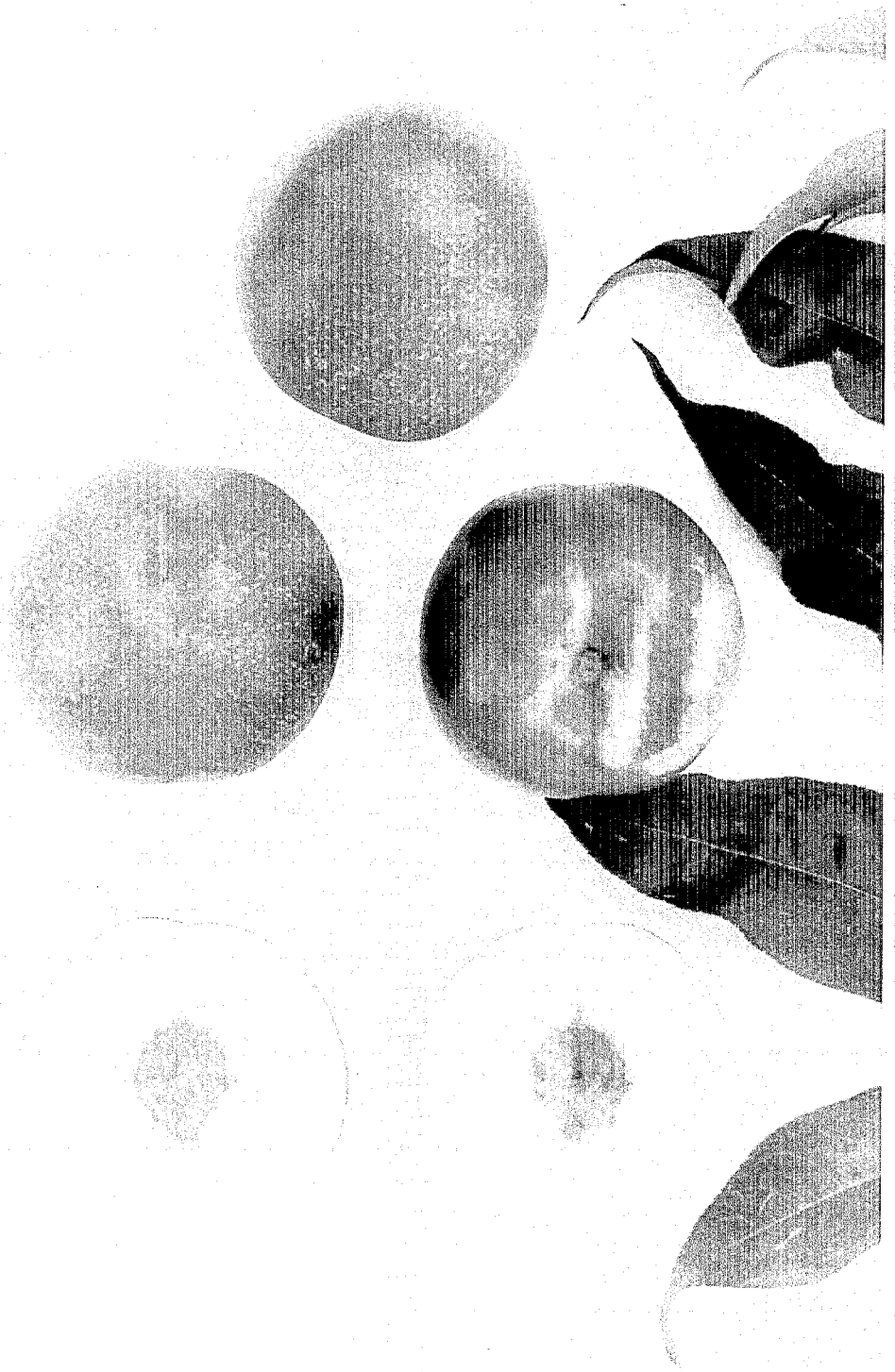

* * * * *